(12) United States Patent
Kühn

(10) Patent No.: US 7,284,905 B2
(45) Date of Patent: Oct. 23, 2007

(54) X-RAY RADIATOR, X-RAY DEVICE AND COMPUTED TOMOGRAPHY APPARATUS WITH FOCUS POSITION DETERMINING CAPABILITY

(75) Inventor: Ulrich Kühn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 2 days.

(21) Appl. No.: 11/141,290

(22) Filed: May 31, 2005

(65) Prior Publication Data

US 2006/0093092 A1    May 4, 2006

(30) Foreign Application Priority Data

Nov. 2, 2004   (DE)  ...................... 10 2004 052 911

(51) Int. Cl.
*H05G 1/04*      (2006.01)
*H01J 35/18*     (2006.01)
*G01D 18/00*     (2006.01)

(52) U.S. Cl. ...................... 378/207; 378/140; 378/119; 378/205

(58) Field of Classification Search ................. 378/16, 378/19, 98.8, 137, 138, 147–153, 205, 207, 378/140, 145, 161; 250/370.09, 370.1
See application file for complete search history.

(56) References Cited

U.S. PATENT DOCUMENTS

| | | | | |
|---|---|---|---|---|
| 3,859,534 A | * | 1/1975 | Loughlin | .................... 378/203 |
| 5,469,429 A | * | 11/1995 | Yamazaki et al. | ............. 378/19 |
| 5,550,886 A | * | 8/1996 | Dobbs et al. | .................. 378/19 |
| 5,550,889 A | * | 8/1996 | Gard et al. | .................. 378/113 |
| 5,583,903 A | * | 12/1996 | Saito et al. | .................... 378/19 |
| 5,657,364 A | * | 8/1997 | Pfoh | ........................... 378/137 |
| 5,745,548 A | * | 4/1998 | Dobbs et al. | ............... 378/207 |
| 6,094,469 A | * | 7/2000 | Dobbs et al. | ................. 378/19 |
| 6,215,844 B1 | * | 4/2001 | Adachi et al. | ................. 378/19 |
| 6,252,935 B1 | * | 6/2001 | Styrnol et al. | ............. 378/137 |
| 6,339,635 B1 | | 1/2002 | Schardt et al. | ............. 378/137 |
| 6,370,218 B1 | * | 4/2002 | Toth et al. | ..................... 378/19 |
| 6,542,576 B2 | | 4/2003 | Mattson | ...................... 378/119 |
| 6,652,143 B2 | * | 11/2003 | Popescu | ..................... 378/207 |
| 2005/0129175 A1 | * | 6/2005 | Shen et al. | .................... 378/62 |
| 2005/0265521 A1 | * | 12/2005 | Deuringer et al. | .......... 378/138 |

FOREIGN PATENT DOCUMENTS

DE     37 09 109 A1     9/1988

* cited by examiner

*Primary Examiner*—Allen C. Ho
(74) *Attorney, Agent, or Firm*—Schiff Hardin LLP

(57) ABSTRACT

An x-ray radiator has a radiator housing from which x-ray radiation originating from a focus is emitted. A pre-diaphragm is disposed in the beam path of the x-ray radiation and has a diaphragm opening in or on the radiator housing. The pre-diaphragm is provided with at least one additional slit through which x-ray radiation can strike on at least one element for determination of the position of the focus. This element is sensitive to x-ray radiation. An x-ray device has such an x-ray radiator and a computed tomography apparatus has such an x-ray device.

6 Claims, 3 Drawing Sheets

X-RAY RADIATOR, X-RAY DEVICE AND COMPUTED TOMOGRAPHY APPARATUS WITH FOCUS POSITION DETERMINING CAPABILITY

BACKGROUND OF THE INVENTION

1. Field of the Invention

The present invention concerns an x-ray radiator with a radiator housing by which x-ray radiation originating from a focus can be emitted. The invention also concerns an x-ray device embodying such an x-ray radiator and a housing adjacent to the radiator housing. The invention also concerns a computed tomography apparatus with such an x-ray device.

2. Description of the Prior Art

X-ray radiators, for example in x-ray diagnostic apparatuses such as a computed tomography apparatus, normally have an x-ray tube containing an anode. In the operation of the x-ray tube, an electron beam emitted by a cathode of the x-ray tube strikes (ideally) a point (the focus) on the anode, with x-ray radiation originating from the focus being emitted. As a consequence of thermal influences or movements of the anode plate of the anode due to mechanical tolerances, during the operation of the x-ray tube the focus can be displaced from its ideal position on the anode plate, which leads to an unwanted displacement of the x-ray radiation originating from the focus. In order to be able to counteract this displacement of the focus, a pre-diaphragm having a diaphragm opening is provided in a diaphragm housing positioned downstream from the x-ray radiator. The pre-diaphragm additionally normally exhibits (relative to the diaphragm opening) two smaller slits through which the x-ray radiation can pass. The x-ray radiation pasting through the two slits strikes elements that are sensitive to x-ray radiation, whereby it is registered which region of the elements is charged with x-ray radiation. The real position of the focus on the anode plate can be determined and compared with the desired position of the focus by a computation device using the signals generated by the elements and based on the known interval relationship between the focus, the pre-diaphragm and the elements. If a deviation of the focus has been determined, the focus, for example, can be displaced back into its desired position by influencing the electron beam originating from the cathode. This normally is achieved by a suitable adjustment of the electromagnetic field influencing the electron beam, this electromagnetic field being generated with coils arranged at the x-ray tube. The computed determines the modified coil currents for this purpose.

The design of such an x-ray radiator 1 and an x-ray device 3 having a diaphragm housing 2 is shown in FIG. 1. The x-ray radiator 1 has a focus F from which an x-ray beam S originates and has a coarse pre-diaphragm 5 in addition to a beam window 4. A second pre-diaphragm 6 is provided with slits as well as elements 7 and 8 for determination of the position of the focus F, and together with the actual main diaphragm 10 for shaping the useful x-ray beam is integrated into the diaphragm housing 2. A scatter radiation seal 9 is additionally present between the x-ray radiator 1 and the diaphragm housing 2 for protection from scatter radiation.

A disadvantage is the relatively large space requirement of the arrangement composed of the x-ray radiator and the diaphragm housing. Due to the space requirement of this arrangement, for a computed tomography apparatus it has not been possible to design the patient opening (the opening in which or through which a patient is located or moved during an examination with an x-ray computed tomography apparatus) to be larger in diameter without enlarging the outer diameter of the rotary frame on which the x-ray radiator and the diaphragm housing are arranged.

SUMMARY OF THE INVENTION

An object of the present invention is to provide an x-ray radiator, an x-ray device as well as a computed tomography apparatus of the described above type wherein the space requirement of the x-ray radiator and the downstream housing is reduced.

According to the invention, this object is achieved by an x-ray radiator with a radiator housing from which x-ray radiation is emitted originating from a focus, with a pre-diaphragm having a diaphragm opening in the beam path of the x-ray radiation being disposed at (i.e., arranged in or on) the radiator housing, the pre-diaphragm being provided with at least one additional slit through which x-ray radiation can proceed to strike at least one element that is sensitive to x-ray radiation, for determination of the position of the focus. Because the diaphragm (which is provided with at least one additional slit) is disposed directly in or on the radiator housing of the x-ray radiator, rather than in a housing downstream from the x-ray radiator, as is conventional, the device formed by the x-ray radiator and the housing downstream from the x-ray radiator be structurally minimized while maintaining a suitable separation relationship between the focus, the pre-diaphragm and the element for determination of the position of the focus, such that the space requirement is markedly reduced relative to the conventional arrangement. With the inventive design of the x-ray radiator it is thus possible to execute the downstream housing smaller, this housing normally containing the element for determination of the position of the focus. The requirements for a computed tomography apparatus, for example to make the patient opening larger with an unchanged outer diameter of the rotary frame, are satisfied in this manner. Not only do fewer patients have a feeling of confinement in the patient opening, but also the space available for medical personnel for medical procedures is enlarged in the region of the patient opening. In addition, the possibility is provided to examine the patient in a different orientation, for example with angled extremities. Moreover, fewer problems result in the examination of persons who exhibit a particularly large corpulence.

In a preferred embodiment of the invention, the pre-diaphragm of the x-ray radiator arranged in or on the radiator housing has two additional slits aligned substantially orthogonally to one another, each being associated with an element that is sensitive to x-ray radiation for determination of the position of the focus. The variation of the position of the focus both in the z-direction (that corresponds to the direction of the system axis of the computed tomography apparatus) and in the $\phi$-direction (that corresponds to the rotational direction of the x-ray acquisition system of the computed tomography apparatus) can be determined with regard to the geometry of the computed tomography apparatus with this arrangement of the slits.

The aforementioned object of the present invention also is achieved by an x-ray device having an x-ray radiator as described above as well as a housing adjacent to or downstream from the radiator housing, in which housing are arranged the element or elements for determination of the position of the focus. According to a variant of the invention, at least one further diaphragm is disposed in the housing in order to shape the usable x-ray beam which should pass through a subject to be examined by the x-ray radiation that passes through the pre-diaphragm. As already mentioned, the housing containing the elements for determination of the position of the focus and the further diaphragms can be made smaller while maintaining the suitable separation relationship between focus, the pre-diaphragm and the elements for determination of the position of the focus, such that the x-ray arrangement composed of x-ray radiator and the additional housing requires a smaller space with the already-mentioned advantages.

According to a further variant of the invention, the x-ray device for determination of the position of the focus has a computation unit connected with the element or elements for determination of the position of the focus, the computation unit calculates the position of the focus from signals generated by the element or the elements for determination of the position of the focus, dependent on the known geometric relationships.

The object also is achieved by a computed tomography apparatus an x-ray device as described above for generation of x-ray radiation, and an x-ray detector associated with the x-ray device, which are arranged opposite one another on a rotary frame that can be rotated around a system axis. Due to the advantageous design of the x-ray device, the computed tomography apparatus can have a patient opening that is enlarged relative to a conventional computed tomography apparatus such that, as mentioned, corpulent persons can be examined without difficulty, and more space is available at the patient opening for medical personnel and new examination procedures are additionally possible at the computed tomography apparatus.

DESCRIPTION OF THE PREFERRED EMBODIMENTS

Figure 2:
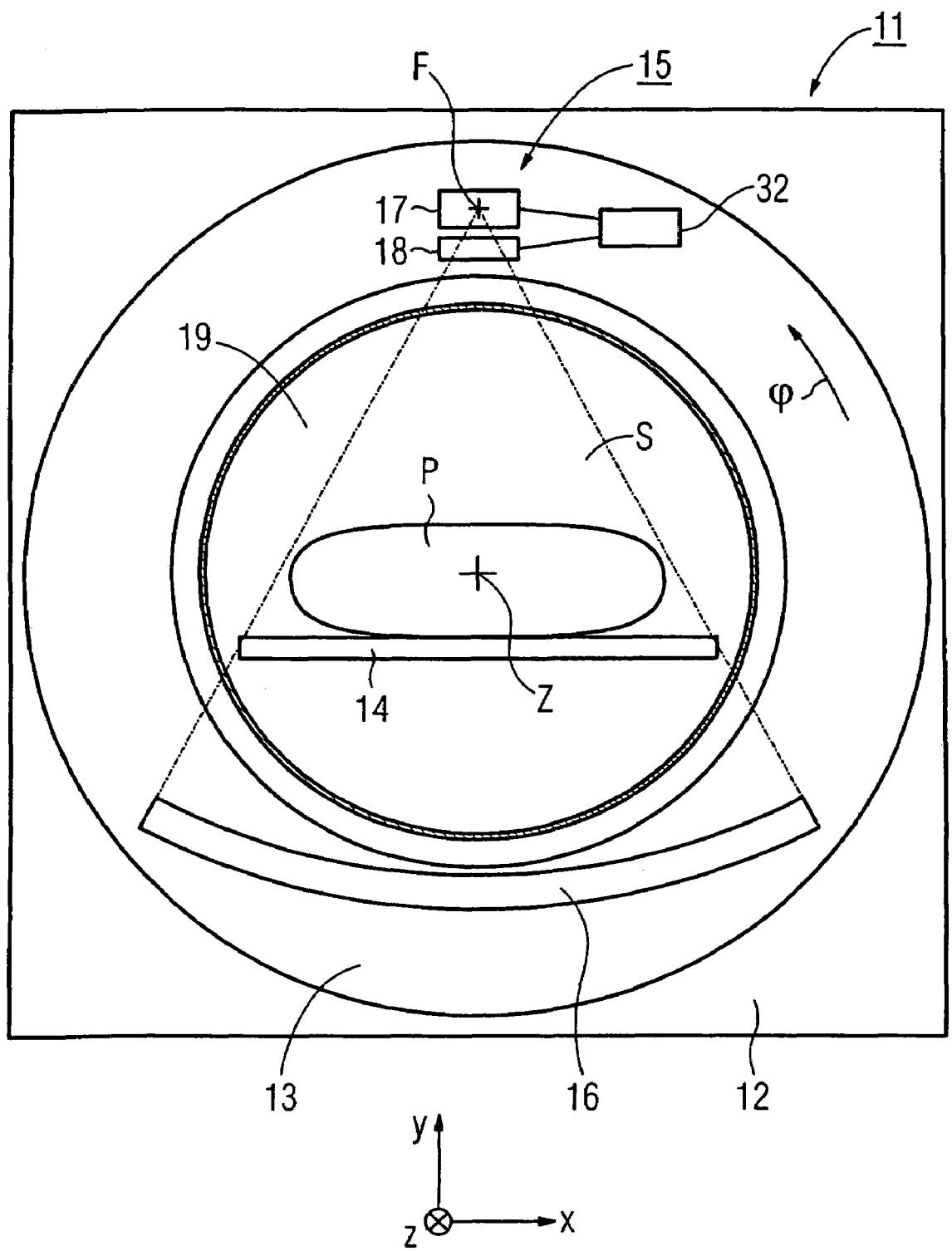
FIG. 2 illustrates a computed tomography apparatus in a simplified representation.

A computed tomography apparatus 11 has a gantry composed of a stationary part 12 and a rotary frame 13 that can be rotated around a system axis Z relative to the stationary part 12, shown in a simplified manner in FIG. 2. Moreover, in FIG. 2 a patient bed 14 is shown in a schematically indicated manner that can be displaced in the direction of the system axis Z during the operation of the computed tomography apparatus 11 in a known manner for examination of a subject, preferably a patient P. Different slice exposures can be obtained given a respectively stationary patient bed 14, as well as spiral exposures with the patient bed 14 with the patient P thereon moving through the patient opening 19 of the computed tomography apparatus 11. An x-ray device 15 and an x-ray detector 16 are disposed opposite one another on the rotary frame 13. During an examination the rotary frame 13 rotates in the (p-direction around the system axis Z, with x-ray radiation originating from a focus F of the x-ray device 15 penetrating a body region of the patient P positioned on the patient bed 14 from different directions, and subsequently strikes the x-ray detector 16, usually a multi-row x-ray detector assembled from a number of detector modules. Slice images or volume images of the acquired body region of the patient P can be reconstructed with a computed (not shown) in a known manner from the acquired x-ray projections and shown on a display (not shown).

Figure 1:
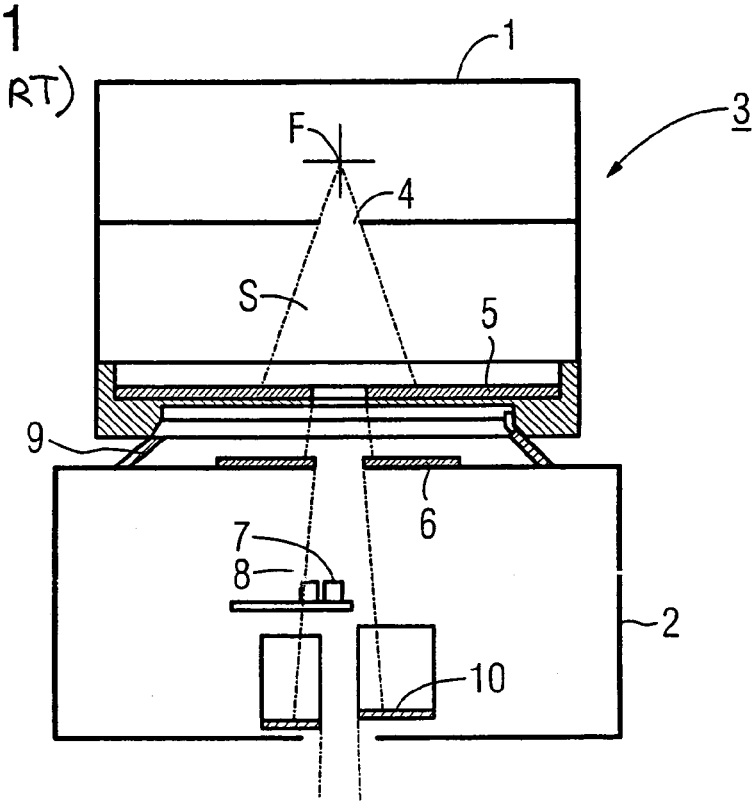
FIG. 1 is a side sectional view of an x-ray device according to the prior art.
Figure 3:
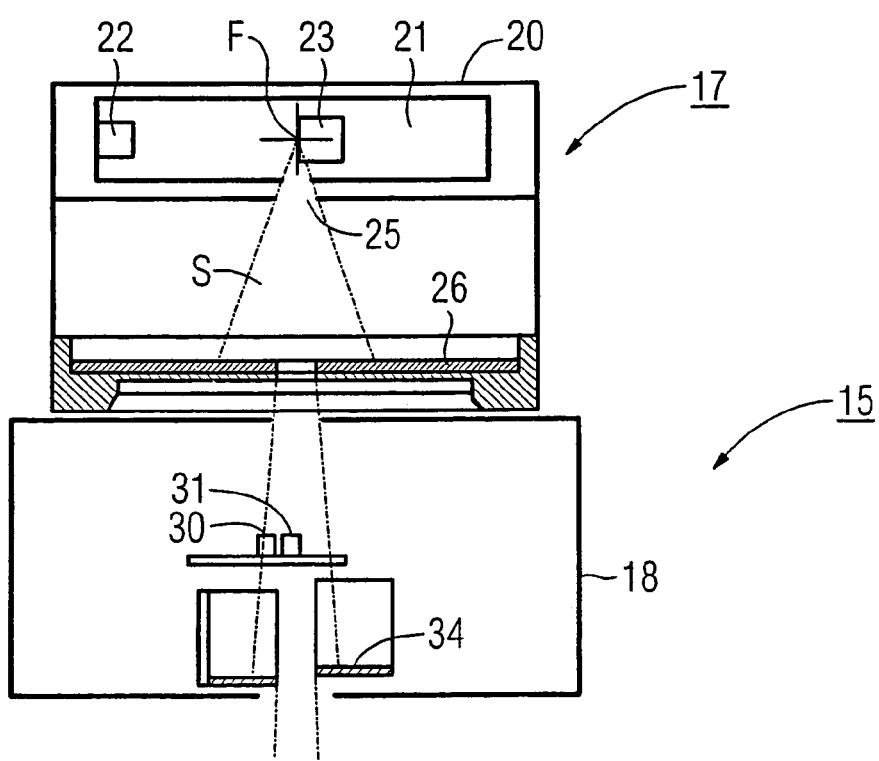
FIG. 3 illustrates an x-ray device with an x-ray radiator of the computed tomography apparatus of FIG. 2, in accordance with the invention.

The design of the x-ray device 15, composed of an x-ray radiator 17 and a diaphragm housing 18, is shown in detail in FIG. 3. As can be seen from FIG. 3, the x-ray radiator 17 has a radiator housing 20 in which (as is schematically indicated in FIG. 3) an x-ray tube 21 is disposed. The focus of the x-ray tube 21 is designated F. The focus F is the point at which the electron beam emanating from a cathode 22 strikes the anode 23 of the x-ray tube 21, from which x-ray radiation S is emitted in the direction of the patient P. To delimit the ray beam of the x-ray radiation S, the x-ray radiator 17 has a beam window 25 in its housing. Furthermore, the x-ray radiator 17 has a pre-diaphragm 26 integrated into the radiator housing 20. The pre-diaphragm 26 shapes the x-ray beam, originating from the focus F and passing through the beam window 25, into a fan shape.

Figure 4:
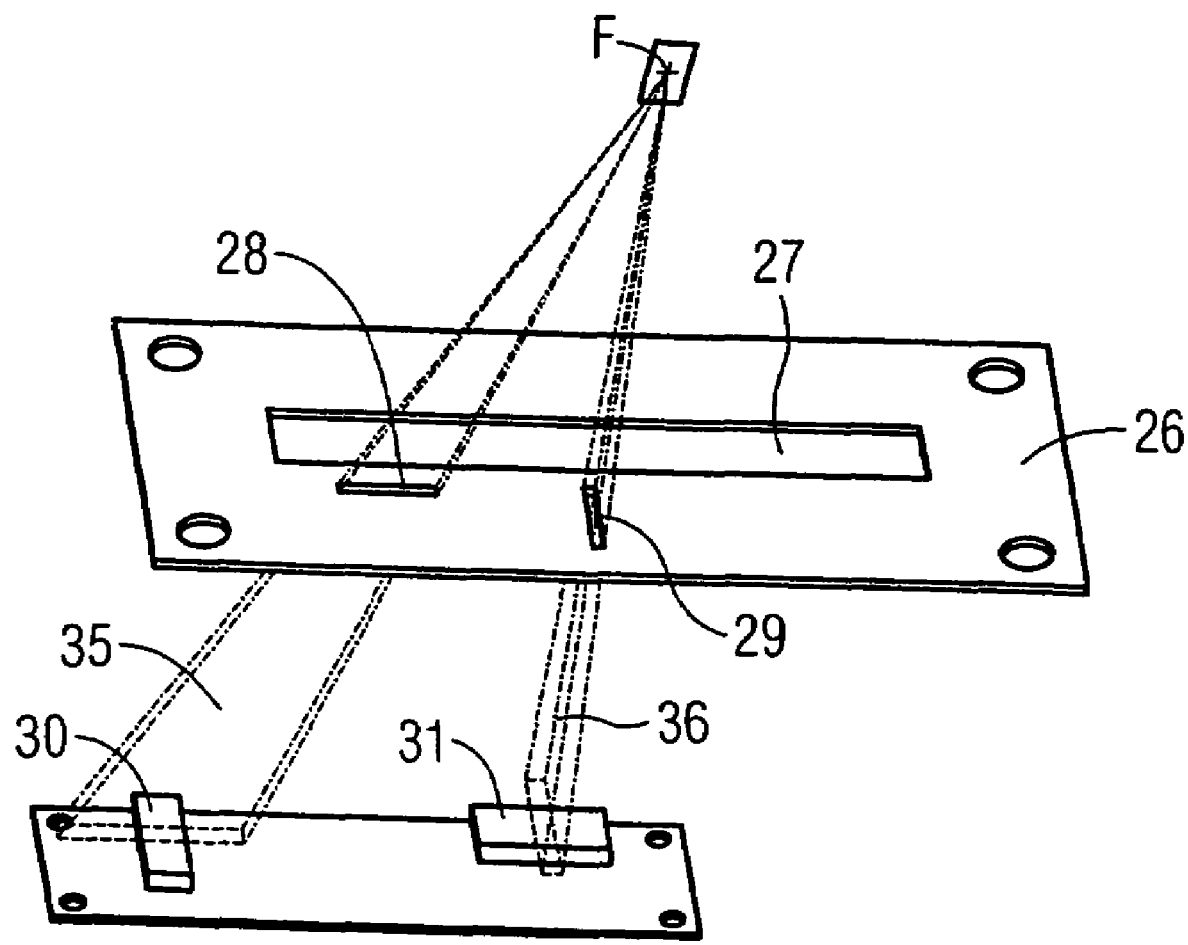
FIG. 4 shows a pre-diaphragm provided with two slits and two elements associated therewith for determination of the position of the focus of the x-ray device of FIG. 3.

The pre-diaphragm 26 is shown in detail in FIG. 4 has a rectangular opening 27 for shaping of the x-ray beam S and is provided with two additional slits 28 and 29 aligned substantially orthogonally to one another, through which slits 28 and 29 x-ray radiation can likewise penetrate. The slits 28, 29 are respectively associated with elements 30, 31 that are sensitive to x-ray radiation for determination of the position of the focus F of the x-ray radiator 17. The elements 30 and 31 are measurement devices sensitive to x-ray radiation. The design of the elements 30, 31 can correspond to the design of detector elements as are used in the x-ray detector 16. Each of the elements 30, 31 has in a known manner a scintillator element for conversion of x-ray radiation into light, downstream from which scintillator element a diode array is normally arranged. The elements 30, 31, however, also can be executed such that they convert radiation directly into electrical signals.

If, in operation of the computed tomography apparatus 11, the anode 23 of the x-ray tube 21 moves (for example in the direction of the system axis Z) due to thermal effects or due to mechanical tolerances of the anode plate (not shown), the position of the focus F on the anode plate thus no longer corresponds to its desired position, which leads to an unwanted variation of the x-ray radiation. Displacement of the focus F, however, also has the effect of causing the x-ray radiation passing through the slits 28 and 29 to expose a different region of the elements 30 and 31 (which are sensitive to x-ray radiation) for determination of the position of the focus F. This position shift causes a change of the signals emitted by the elements 30 and 31 for determination of the position of the focus F. As is schematically shown in FIG. 2, the elements 30 and 31 are connected to a computer 32, for example a PC that can calculate the change of the position of the focus F from the signals provided by the elements 30 and 31 and influence the x-ray tube 21 of the x-ray radiator 17 such that the focus F is moved back from its real position to its desired position. Generally this happens by modifying the electromagnetic field that deflects the electron beam emitted by the cathode 22 of the x-ray tube 21 in the direction of the anode 23 such that the electron beam again strikes the desired position on the anode plate of the anode 23 of the x-ray tube 21, For this purpose, the coil currents of coils (not shown in detail in the figures) associated with the x-ray tube 21 are modified in a suitable manner by the computer 32. An x-ray tube allowing such a procedure is described in German PS 198 10 346.

It is also clear that a deviation of the focus F from its desired position can be determined by means of the slits 28 and 29 as well as with the aid of the elements 30 and 31, and regulation can ensue via the computer 32 such that the focus F, when it has deviated from its desired position, can be directed back to this position again. For this purpose, in the inventive x-ray radiator 17 the pre-diaphragm 26 is integrated into the housing 20 of the x-ray radiator 17. Moreover, as shown in FIG. 3, the elements 30 and 31 for determination of the position of the focus F are disposed in a further housing 18 downstream from the x-ray radiator 17. This design allows displacements of the focus F (associated with deflections of the x-ray beam 35, 36 passing through the slots 28, 29 (as designated by the dashed lines) from their zero position shown in FIG. 4) can be accurately detected and corrected while maintaining the distance relationships between focus F, the pre-diaphragm 26 and the elements 30, 31 for determination of the position of the focus F, which distance relationships are necessary for the regulation of the position of the focus F. While the element 30 serves to establish displacement in the z-direction, displacement in the φ-direction can be registered with the element 31.

In addition to the elements 30, 31 for determination of the position of the focus F, a known, adjustable diaphragm 34 is disposed in the housing 18, with which a usable x-ray beam that penetrates the patient P to be examined can be shaped again from the already pre-shaped x-ray beam S.

The inventive design of the x-ray radiator 17 arranged in the additional housing 18 allows the x-ray radiator 17 to be advanced closer to the focus F, such that overall the x-ray device 15 composed of the x-ray radiator 17 and the housing 18 can be realized with a smaller volume. In particular the height of the housing 18 can be reduced.

In contrast to the conventional x-ray device, in the inventive x-ray device no protection device for the scatter radiation between the x-ray radiator 17 and the housing 18 is necessary due to the integration of the pre-diaphragm 26 into the radiator housing 20. Moreover, the second pre-diaphragm 6 that is necessary in the conventional x-ray device can be foregone. The most important aspect is, however, that the space requirement of the inventive x-ray arrangement is less than that of the conventional x-ray arrangement, such that the patient opening 19 of the computed tomography apparatus 11 can be increased. Not only is more space available for the positioning of patients and for medical personnel working at the computed tomography apparatus 11, but also additional examination possibilities for patients can be considered, since now more limbs of patients can be positioned differently due to the increased available space.

The pre-diaphragm 26 does not necessarily have to contain two slits. Particularly when deviations of the focus F are only to be expected in one direction, the second slit can be omitted.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray radiator comprising:
   an x-ray source that emits x-ray radiation emanating from a focus;
   a radiator housing in which said x-ray source is contained;
   a pre-diaphragm formed by a unitary structure that is integrated into the radiator housing and that is disposed in a beam path of said x-ray radiation at said housing, said pre-diaphragm unitary structure comprising a diaphragm opening through which said x-ray radiation proceeds and a pre-diaphragm slit, separate from said opening, through which said x-ray radiation also proceeds; and
   an x-ray sensitive element on which x-ray radiation proceeding through said slit is incident, for emitting an electrical signal for determining a position of said focus.

2. An x-ray radiator as claimed in claim 1 wherein said slit is a first slit and wherein said x-ray sensitive element is a first x-ray sensitive element, and wherein said pre-diaphragm has a second slit, substantially orthogonal to said first slit, also allowing passage of said x-ray radiation therethrough, and a second x-ray sensitive element on which said x-ray radiation passing through said second slit is incident, said second x-ray sensitive element also generating electrical signals for determining said position of said focus.

3. An x-ray device comprising:
   an x-ray radiator comprising an x-ray source that emits x-ray radiation emanating from a focus, a radiator housing in which said x-ray source is contained, and a pre-diaphragm formed by a unitary structure that is integrated into the radiator housing and that is disposed in a beam path of said x-ray radiation at said housing, said pre-diaphragm unitary structure comprising a diaphragm opening through which said x-ray radiation proceeds and a pre-diaphragm slit, separate from said opening, through which said x-ray radiation also proceeds;
   an x-ray sensitive element on which x-ray radiation proceeding through said slit is incident, for emitting an electrical signal for determining a position of said focus; and
   a further housing adjacent to said radiator housing in which said x-ray sensitive element is disposed.

4. An x-ray device as claimed in claim 3 comprising a primary radiation diaphragm disposed in said further housing.

5. An x-ray device as claimed in claim 3 comprising a computation unit electrically connected to said x-ray sensitive element for receiving said electrical signals therefrom, said computation unit calculating said position of said focus from said signals.

6. An x-ray computed tomography apparatus comprising:
   a rotary frame;
   an x-ray radiator and a radiation detector mounted on said rotary frame opposite each other;
   said x-ray radiator comprising an x-ray source that emits x-ray radiation emanating from a focus, a radiator housing in which said x-ray source is contained, and a pre-diaphragm formed by a unitary structure that is integrated into the radiator housing and that is disposed in a beam path of said x-ray radiation at said housing, said pre-diaphragm unitary structure comprising a diaphragm opening through which said x-ray radiation proceeds and a pre-diaphragm slit, separate from said opening, through which said x-ray radiation also proceeds; and
   an x-ray sensitive element on which x-ray radiation proceeding through said slit is incident, for emitting an electrical signal for determining a position of said focus.

* * * * *